(12) United States Patent
Delli-Santi

(10) Patent No.: US 8,147,505 B2
(45) Date of Patent: Apr. 3, 2012

(54) SURGICAL INSTRUMENT FOR MANIPULATING SURGICAL SUTURE AND METHODS OF USE

(75) Inventor: George Delli-Santi, Scotts Valley, CA (US)

(73) Assignee: ArthroCare Corporation, Austin, TX (US)

( * ) Notice: Subject to any disclaimer, the term of this patent is extended or adjusted under 35 U.S.C. 154(b) by 407 days.

(21) Appl. No.: 12/408,773

(22) Filed: Mar. 23, 2009

(65) Prior Publication Data

US 2010/0241144 A1 Sep. 23, 2010

(51) Int. Cl.
 *A61B 17/04* (2006.01)
 *A61B 17/12* (2006.01)

(52) U.S. Cl. .................................................. 606/144
(58) Field of Classification Search .............. 606/139, 606/144–148; 112/169
See application file for complete search history.

(56) References Cited

U.S. PATENT DOCUMENTS

| | | | |
|---|---|---|---|
| 919,138 A | 4/1909 | Drake et al. ................. 606/144 |
| 1,635,066 A | 7/1927 | Wells ........................... 606/145 |
| 2,269,963 A | 1/1942 | Wappler ....................... 604/61 |
| 2,286,578 A | 6/1942 | Sauter .......................... 606/148 |
| 2,327,353 A * | 8/1943 | Karle ........................... 606/146 |
| 2,737,954 A * | 3/1956 | Knapp .......................... 606/146 |
| 2,738,790 A | 3/1956 | Todt, Sr. et al. ............ 606/145 |
| 3,842,840 A | 10/1974 | Schweizer .................. 128/334 |
| 3,946,740 A | 3/1976 | Bassett ........................ 128/334 |
| 4,027,608 A * | 6/1977 | Arbuckle ..................... 112/169 |
| 4,109,658 A | 8/1978 | Hughes ........................ 128/340 |
| 4,164,225 A | 8/1979 | Johnson ....................... 128/334 |
| 4,235,177 A * | 11/1980 | Arbuckle ..................... 112/169 |
| 4,345,601 A | 8/1982 | Fukuda ........................ 128/339 |
| 4,373,530 A | 2/1983 | Kilejian ...................... 128/334 R |
| 4,484,580 A * | 11/1984 | Nomoto et al. .............. 606/146 |
| 4,493,323 A | 1/1985 | Albright et al. ............. 128/340 |
| 4,621,640 A * | 11/1986 | Mulhollan et al. .......... 606/144 |
| 4,635,637 A | 1/1987 | Schreiber ..................... 128/337 |
| 4,738,255 A | 4/1988 | Goble et al. ............. 128/92 YF |
| 4,741,330 A | 5/1988 | Hayhurst .................... 128/43 R |
| 4,781,182 A | 11/1988 | Purnell et al. ................ 128/92 |
| 4,836,205 A | 6/1989 | Barrett ......................... 128/340 |
| 4,923,461 A | 5/1990 | Caspari ........................ 606/146 |
| 4,926,860 A | 5/1990 | Stice et al. ................... 606/146 |

(Continued)

FOREIGN PATENT DOCUMENTS

CA 2205176 12/2000

(Continued)

OTHER PUBLICATIONS

UK Search Report for GB 1019353.0 4pgs.

(Continued)

*Primary Examiner* — Corrine M McDermott
*Assistant Examiner* — Dianne Dornbusch
(74) *Attorney, Agent, or Firm* — Matthew Scheele; Brian Szymczak

(57) ABSTRACT

A surgical instrument and method for manipulating surgical suture during minimally invasive surgical procedures. Surgical instrument includes an elongate body with a handle at the elongate body's proximal end. Elongate body also includes a distal portion, a longitudinal axis and an outer surface, and the distal portion includes at least one moveable wire. This wire moves so as to selectively capture and release a suture and suture purchase may be substantially obtained between the wire and the elongate body outer surface. The instrument also includes an actuation mechanism connecting the handle to the wire. The wire is moved via the actuation mechanism and a substantial component of the motion of the wire is eccentric rotation.

24 Claims, 8 Drawing Sheets

U.S. PATENT DOCUMENTS

| | | | |
|---|---|---|---|
| 4,935,027 A | 6/1990 | Yoon | 606/146 |
| 4,957,498 A | 9/1990 | Caspari | 606/146 |
| 4,981,149 A | 1/1991 | Yoon et al. | 128/898 |
| 5,037,422 A | 8/1991 | Hayhurst et al. | 606/72 |
| 5,037,433 A | 8/1991 | Wilk et al. | 606/139 |
| 5,046,513 A | 9/1991 | Gatturna et al. | 128/898 |
| 5,059,201 A | 10/1991 | Asnis | 606/144 |
| 5,085,661 A | 2/1992 | Moss | 606/139 |
| 5,152,769 A * | 10/1992 | Baber | 606/145 |
| 5,217,471 A | 6/1993 | Burkhart | 606/148 |
| 5,222,977 A | 6/1993 | Esser | 606/223 |
| 5,269,786 A | 12/1993 | Morgan | 606/96 |
| 5,304,184 A | 4/1994 | Hathaway et al. | 606/144 |
| 5,312,422 A | 5/1994 | Trott | 606/144 |
| 5,318,577 A | 6/1994 | Li | 606/147 |
| 5,336,229 A | 8/1994 | Noda | 606/144 |
| 5,356,424 A * | 10/1994 | Buzerak et al. | 606/223 |
| 5,397,325 A | 3/1995 | Della Badia et al. | 112/169 |
| 5,403,329 A | 4/1995 | Hinchcliffe | 606/147 |
| 5,409,494 A | 4/1995 | Morgan | 606/96 |
| 5,417,699 A | 5/1995 | Klein et al. | 606/139 |
| 5,431,666 A | 7/1995 | Sauer et al. | 606/139 |
| 5,445,167 A | 8/1995 | Yoon et al. | 128/898 |
| 5,454,823 A | 10/1995 | Richardson et al. | 606/148 |
| 5,474,565 A | 12/1995 | Trott | 606/144 |
| 5,480,405 A | 1/1996 | Yoon | 606/139 |
| 5,499,991 A | 3/1996 | Garman et al. | 606/148 |
| 5,501,688 A * | 3/1996 | Whiteside et al. | 606/103 |
| 5,522,820 A | 6/1996 | Caspari et al. | 606/148 |
| 5,527,322 A | 6/1996 | Klein et al. | 606/144 |
| 5,540,705 A * | 7/1996 | Meade et al. | 606/145 |
| 5,573,542 A | 11/1996 | Stevens | 606/144 |
| 5,575,801 A | 11/1996 | Habermeyer et al. | 606/144 |
| 5,609,597 A | 3/1997 | Lehrer | 606/139 |
| 5,613,974 A | 3/1997 | Andreas et al. | 606/144 |
| 5,618,290 A | 4/1997 | Toy et al. | 606/139 |
| 5,626,590 A | 5/1997 | Wilk | 606/148 |
| 5,645,552 A | 7/1997 | Sherts | 606/145 |
| 5,653,717 A * | 8/1997 | Ko et al. | 606/144 |
| 5,665,108 A | 9/1997 | Galindo | 606/215 |
| 5,690,653 A | 11/1997 | Richardson et al. | 606/148 |
| 5,700,273 A | 12/1997 | Buelna et al. | 606/148 |
| 5,741,281 A | 4/1998 | Martin | 606/148 |
| 5,776,150 A | 7/1998 | Nolan et al. | 606/148 |
| 5,779,719 A | 7/1998 | Klein et al. | 606/144 |
| 5,792,151 A | 8/1998 | Heck et al. | 606/144 |
| 5,792,152 A | 8/1998 | Klein et al. | 606/144 |
| 5,792,153 A | 8/1998 | Swain et al. | 606/144 |
| 5,797,927 A | 8/1998 | Yoon | 606/144 |
| 5,836,956 A | 11/1998 | Buelna et al. | 606/148 |
| 5,860,991 A | 1/1999 | Klein et al. | 606/145 |
| 5,860,992 A | 1/1999 | Daniel et al. | 606/145 |
| 5,902,311 A | 5/1999 | Andreas et al. | 606/144 |
| 5,904,692 A | 5/1999 | Steckel et al. | 606/139 |
| 5,908,426 A | 6/1999 | Pierce | 606/139 |
| 5,921,994 A | 7/1999 | Andreas et al. | 606/144 |
| 5,947,982 A | 9/1999 | Duran | 606/139 |
| 5,954,733 A * | 9/1999 | Yoon | 606/147 |
| 5,957,937 A * | 9/1999 | Yoon | 606/147 |
| 5,980,538 A | 11/1999 | Fuchs et al. | 606/145 |
| 5,984,933 A | 11/1999 | Yoon | 606/148 |
| 6,001,109 A | 12/1999 | Kontos | 606/148 |
| 6,022,360 A | 2/2000 | Reimels et al. | 606/144 |
| 6,024,747 A | 2/2000 | Kontos | 606/148 |
| 6,036,699 A | 3/2000 | Andreas et al. | 606/139 |
| 6,048,351 A | 4/2000 | Gordon et al. | 606/144 |
| 6,051,006 A | 4/2000 | Shluzas et al. | 606/148 |
| 6,059,801 A | 5/2000 | Samimi | 606/144 |
| 6,096,051 A | 8/2000 | Kortenbach et al. | 606/144 |
| 6,117,144 A | 9/2000 | Nobles et al. | 606/144 |
| 6,136,010 A | 10/2000 | Modesitt et al. | 606/144 |
| 6,143,004 A | 11/2000 | Davis et al. | 606/144 |
| 6,143,005 A * | 11/2000 | Yoon et al. | 606/148 |
| 6,214,028 B1 * | 4/2001 | Yoon et al. | 606/205 |
| 6,217,592 B1 | 4/2001 | Freda et al. | 606/145 |
| 6,245,079 B1 | 6/2001 | Nobles et al. | 606/144 |
| 6,332,889 B1 | 12/2001 | Sancoff et al. | 606/148 |
| 6,533,795 B1 | 3/2003 | Tran et al. | 606/144 |
| 6,551,330 B1 | 4/2003 | Bain et al. | 606/144 |
| 6,605,096 B1 | 8/2003 | Ritchart | 606/144 |
| 6,770,084 B1 | 8/2004 | Bain et al. | 606/144 |
| 6,893,448 B2 | 5/2005 | O'Quinn et al. | 606/139 |
| 6,896,686 B2 | 5/2005 | Weber | 606/145 |
| 6,911,034 B2 | 6/2005 | Nobles et al. | 606/144 |
| 6,923,819 B2 * | 8/2005 | Meade et al. | 606/144 |
| 6,984,237 B2 | 1/2006 | Hatch et al. | 606/139 |
| 7,004,951 B2 * | 2/2006 | Gibbens, III | 606/144 |
| 7,090,686 B2 | 8/2006 | Nobles et al. | 606/144 |
| 7,112,208 B2 | 9/2006 | Morris et al. | 606/144 |
| 7,160,309 B2 * | 1/2007 | Voss | 606/144 |
| 7,169,157 B2 * | 1/2007 | Kayan | 606/148 |
| 7,198,631 B2 | 4/2007 | Kanner et al. | 606/139 |
| 7,377,926 B2 | 5/2008 | Topper et al. | 606/144 |
| 7,449,024 B2 | 11/2008 | Stafford | 606/144 |
| 7,544,199 B2 | 6/2009 | Bain et al. | 606/144 |
| 7,585,305 B2 | 9/2009 | Dreyfuss | 606/144 |
| 7,758,597 B1 | 7/2010 | Tran et al. | 606/144 |
| 7,879,048 B2 | 2/2011 | Bain et al. | 606/144 |
| 2002/0147456 A1 | 10/2002 | Diduch et al. | 606/144 |
| 2003/0065337 A1 | 4/2003 | Topper et al. | 606/144 |
| 2003/0195528 A1 | 10/2003 | Ritchart | 606/144 |
| 2003/0233106 A1 | 12/2003 | Dreyfuss | 606/144 |
| 2004/0010273 A1 | 1/2004 | Diduch et al. | 606/144 |
| 2004/0127913 A1 * | 7/2004 | Voss | 606/108 |
| 2004/0236353 A1 | 11/2004 | Bain et al. | 606/139 |
| 2004/0249394 A1 | 12/2004 | Morris et al. | 606/144 |
| 2005/0055038 A1 * | 3/2005 | Kelleher et al. | 606/151 |
| 2005/0165419 A1 | 7/2005 | Sauer et al. | 606/148 |
| 2008/0097482 A1 | 4/2008 | Bain et al. | 606/144 |
| 2011/0118760 A1 | 5/2011 | Gregoire et al. | 606/145 |

FOREIGN PATENT DOCUMENTS

| | | |
|---|---|---|
| DE | 4235602 A1 | 4/1994 |
| DE | 2532242 A1 | 7/1995 |
| EP | 0535906 A2 | 4/1993 |
| EP | 1408849 B1 | 12/2010 |
| WO | 91/06247 | 5/1991 |
| WO | 97/10756 | 3/1997 |
| WO | 03/028532 | 4/2003 |
| WO | 10/111176 | 9/2010 |

OTHER PUBLICATIONS

PCT International Search Report for PCT/US01/42186 3 pgs, mailed Feb. 13, 2002.
PCT International Preliminary Examination Report for PCT/US01/42186 3pgs, Sep. 9, 2003.
PCT International Search Report for PCT/US02/22889 2 pgs, mailed May 8, 2003.
PCT International Preliminary Examination Report for PCT/US02/22889 3 pgs, Jan. 15, 2003.
PCT International Search Report for PCT/US03/18540 1 pg, mailed Oct. 15, 2003.
PCT International Preliminary Examination Report for PCT/US03/18540 4 pgs, Aug. 24, 2004.
European Search Report for EP 02752446 5pgs, Oct. 12, 2009.
European Examination Report for EP 037419405 4pgs, Jan. 11, 2010.

* cited by examiner

US 8,147,505 B2

SURGICAL INSTRUMENT FOR MANIPULATING SURGICAL SUTURE AND METHODS OF USE

TECHNICAL FIELD

The present invention relates generally to surgical methods and instrumentation, and more particularly to a minimally invasive instrument adapted to retrieve and release surgical suture during a surgical procedure.

BACKGROUND OF THE INVENTION

With the advent of endoscopic surgery, a significant number of minimally invasive instruments have been developed to facilitate these advantageous procedures. The term "endoscopy" is used to include many procedures where minimally invasive techniques and surgery is undertaken within a patient cavity or hollow organ, and may include arthroscopy, laparoscopy and percutaneous approaches to name just some.

As with many minimally invasive instruments, devices tend to have small elongate bodies designed to travel through a portal or through the patient's skin or tissue, into and out of a cavity. The smaller the elongate body, the less traumatic the instrument is to the patient and the better the potential procedural outcome. The challenge often faced is to design an endoscopic instrument that has useful function while being small.

Many suture graspers or suture retrievers are, in general terms forceps or graspers at the end of a long narrow tube, with fairly complicated mechanisms confined to a small envelope. These mechanisms may have multiple small linkages and components, limited in size. There is often a tradeoff as to the strength of an instrument of this nature and the physical size of it. It is considered desirable to have as small an instrument as possible, but strong enough to perform its function. Other tradeoffs in size significantly impact the instrument's complexity or cost and significantly compromise the instrument's durability. In addition in order to open the instrument jaws, tissue within the patient cavity may need to be moved out of the way. This may be difficult or cause unneeded trauma to the patient. Depending on the instrument's strength, surrounding tissue may also restrict the graspers from opening.

BRIEF SUMMARY OF THE INVENTION

Therefore a need has arisen for a small, cost effective and easy to use instrument to capture, move and release surgical suture during an endoscopic surgical procedure.

The present disclosure presents a surgical instrument for manipulating surgical suture within a patient cavity or hollow organ including an elongate body with a proximal end, a distal portion, a longitudinal axis and an outer surface. The proximal portion includes a handle and the distal portion includes at least one moveable wire operable to selectively capture and release a suture, the wire having a free end and a connected portion and an arcuate portion therebetween. The instrument also includes an actuation mechanism that is connected between the handle and the wire connected portion and may selectively move the wire, wherein the wire's motion may be characterized as eccentric rotation.

In another aspect, a surgical instrument is disclosed for manipulating a surgical suture including an elongate body with a proximal end, a distal portion, a longitudinal axis and an outer surface. The proximal end includes a handle and the distal portion includes at least one moveable wire that selectively captures and releases a suture. This wire has a free end and a connected portion and an arcuate portion therebetween and selectively captures sutures in a space defined as between the wire and the elongate body outer surface. This instrument also includes an actuation mechanism to deploy the wire as necessary.

In another aspect, a method of performing a surgical procedure on a body is disclosed. The method includes positioning an elongate body in proximity to a suture, the elongate body having an outer surface and a moveable wire and an actuation mechanism disposed therein. The moveable wire is then eccentrically rotated using actuation mechanism, such that the moveable wire is deployed outside the elongate body. The suture is then captured. The suture may then be moved to a desired location before retracting the moveable wire so as to release the suture.

In another aspect, a method of performing a surgical procedure on a body is disclosed. The method includes positioning an elongate body in proximity to a suture, the elongate body having an outer surface and a moveable wire and an actuation mechanism disposed therein. The moveable wire is then moved using the actuation mechanism, such that the moveable wire is deployed outside the elongate body. The suture is then captured between the wire and the elongate body outer surface. The suture may then me moved to a desired location before retracting the moveably wire so as to release the suture.

The present disclosure preferably allows for a mechanism for wire deployment that is simple, resulting in a smaller instrument size and a small opening in the patient. This may reduce the trauma to the patient and potentially improve the patient's recovery. Additionally, the device according to the present disclosure preferably does not include graspers and therefore the instrument does not need to move as much surrounding tissue out of the way in order to access the suture. Furthermore, the presently described device allows for the suture to be easily put in position. The suture may be approached so that the instrument is placed along the side of the suture before wire deployment and suture capture. Placing a suture alongside an instrument is a relatively easy operation when viewed endoscopically in two dimensions, compared with placing a suture at the tip of an instrument.

DETAILED DESCRIPTION OF THE INVENTION

Figure 1A:
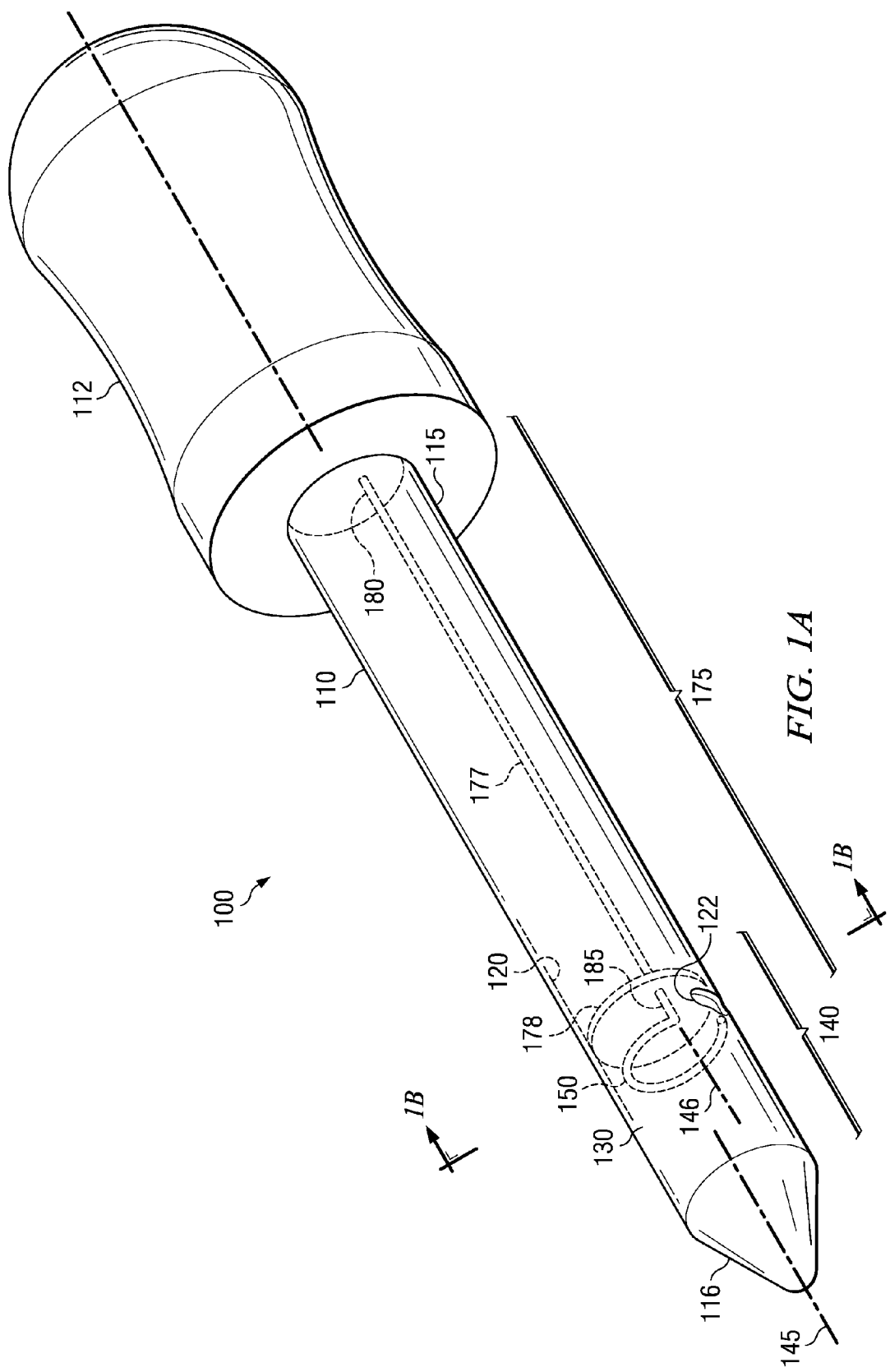
FIG. 1A shows a surgical instrument according to the teachings of the present disclosure.

Before the various embodiments are described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The instruments according to the presently described embodiments may be configured to address any application wherein a surgical suture needs to be manipulated during a minimally invasive surgical procedure. Manipulation includes suture capture, transfer and release, during a minimally invasive procedure.

FIG. 1A shows a surgical instrument 100 according to the teachings of the present disclosure. Instrument 100 is operable to capture and release a suture (not shown here) using a wire 150 placed toward the distal portion 140. Instrument 100 includes elongate body 110 and handle 112, located at the elongate body proximal end 115. In the present embodiment elongate body 110 has a diameter in the range of 0.5-5 mm and preferably in the range of 1-3 mm. The smaller the size of instrument 100 the less trauma this may cause to the patient.

Elongate body 110 also includes a distal portion 140, a generally smooth outer surface 130, a longitudinal axis 145 and, in the present embodiment a hollow lumen 120. Distal portion 140 includes a distal tip 116 which may be generally smooth and formed to be atraumatic to the patient. Alternative embodiments may include a more traumatic distal tip 116 to provide a surgeon with dissection, tissue piercing or cutting capabilities.

Instrument 100 may be operable to insert into a cannula (not shown here). A cannula may provide the portal into a patient cavity or hollow organ. With the use of a cannula, distal tip 116 need not necessarily be traumatic or sharp in order to access a patient cavity. In the present embodiment instrument 100 is shown with a straight distal portion 140. In alternative embodiments, distal portion 140 may be curved or angled relative to body longitudinal axis 145. A curve may make it easier to place a suture in the right position along the body 110, if the capture location is in the curve's concave portion, for example. Curved instruments or curves tips may also provide the surgeon a feeling of adding a dimension to the two dimensional monitor or screen during endoscopic imaging, giving the surgeon a better perspective to work with during surgery. This makes locating instruments and objects such as sutures easier to place relative to each other.

Elongate body distal portion 140 also includes at least one moveable wire 150 and at least one lateral aperture 122. Wire 150 is moveable and may be moved from within elongate body lumen 120 through aperture 122 so that it is substantially outside elongate body distal portion 140. In this embodiment wire 150 is moved so that wire 150 eccentrically rotates about axis 145. Wire 150 may also be returned from being substantially outside lumen 120 to substantially inside lumen 120 to release a suture (not shown here). Rotation of wire 150 may preferably be substantially perpendicular to longitudinal axis 145. In other potential embodiments wire 150 may nutate around an axis, such as one that is parallel to axis 145.

In circumstances where the instrument 100 is not being employed to capture a suture (not shown here), in devices according to the present embodiments the wire 150 would preferably be located in a position that does not significantly interrupt the outer surface 130 of elongate body 110, or that may create a significant obstacle that may cause interference with surrounding patient tissue during instrument manipulation. For example, during instrument insertion into a cannula or through an opening, the outer surface 130 is preferably uninterrupted. During deployment, wire 150 is moved in such a way as to travel away from the outer surface 130 to loop over suture (shown in FIG. 2) and thereby capture any suture that is placed close to aperture 122. Suture is captured using the wire 150 and outer surface 130 as the capture boundary.

Wire 150 may be flexible or rigid and may be constructed from any suitable biocompatible material. A more rigid wire 150 may provide improved suture capture, as the intended trajectory and shape of the wire 150 may be better maintained and a more rigid wire 150 may also maintain a better contact with suture to push suture against outer surface 130 and provide better capture. A more rigid wire 150 may also be able to move any surrounding tissue away during deployment of wire 150. Wire 150 is shown curved along one plane only. Alternate wire embodiments may be coil shaped with a varying curve. Wire 150 may also include multiple revolutions or be helical in shape and therefore have a longitudinal axis (not shown here). In the present embodiment wire 150 is shown with a circular cross section and generally smooth outer surface. In alternative embodiments, wire may have alternative cross sections with flat portions with may improve wire purchase. Portions of wire outer surface may not necessarily be smooth, whereby a rough or high friction surface may improve suture capture. Aperture 122 is located, sized and shaped for easy motion of wire 150 from inside lumen 120 to outside surface 130. However, aperture 122 is preferably sized to limit width and length such that patient tissue or blood is not allowed to enter elongate body lumen 120 and potentially interfere with the motion of the wire 150.

In the present embodiment one wire 150 is shown. Alternative embodiments may include multiple wires 150 and correlating apertures 122, which may be rotated in substantially similar or substantially opposing directions. Multiple wires 150 may gain better purchase on suture, or leave the surgeon more room for maneuvering a suture into the correct position and/or may make suture location less restrictive or more easily accomplished.

Wire 150 is moved using an actuation mechanism 175. In the present embodiment actuation mechanism 175 includes at least one pivot support 178, and at least one actuation rod 177, the actuation rod 177 having a proximal handle end 180 and a distal wire end 185. Handle 112 is preferably connected to actuation rod handle end 180 and wire 150 is preferably connected to distal wire end 185 so that movement of handle 112 may manipulate wire 150 along a desired trajectory. In the present embodiment the user may preferably twist or turn handle 112 to rotate actuation rod 177 and thereby rotate wire 150 about axis 146 to travel through aperture 122.

Alternate handle embodiments may have a trigger handle (not shown here) whereby pulling a trigger may deploy wire 150. Axis 146 is shown parallel to body longitudinal axis 145 and offset a predetermined radial distance to cause wire to eccentrically rotate about longitudinal axis 145. In an alternative embodiment, not shown here, axis 146 may be unparallel to or placed at an angle to axis 145 to nutate or oscillate wire 150 in an alternate motion during deployment. In further alternative actuation embodiments actuation rod 177 may slide along a curved cam slot (not shown here) located in pivot support 178 to both rotate and translate wire 150 eccentrically about longitudinal axis 145. This may create an alternate path through aperture 122.

Figure 1B:
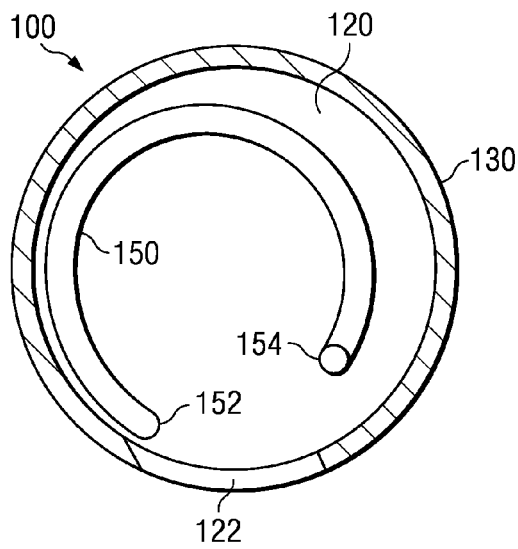
FIG. 1B shows a cross sectional view of surgical instrument according to the teachings of the present disclosure.

FIG. 1B shows a cross section of instrument 100 with wire 150 positioned within lumen 120 before or after deployment. Wire 150 has a connected portion 154 that is connected to actuation mechanism 175 (shown in FIG. 1A). Wire free end 152 travels through aperture 122 during wire deployment, and wire free end 152 may be smooth so as to not cause trauma to patient, or snag on patient tissue or suture during suture capture. Wire 150 is preformed to be shaped in a substantially continuous curve between said free end 152 and said connected portion 154. Curve may be substantially circular or may be a more complex and varying curve to accomplish easy travel through aperture 122 and good purchase on suture.

Figure 2B:
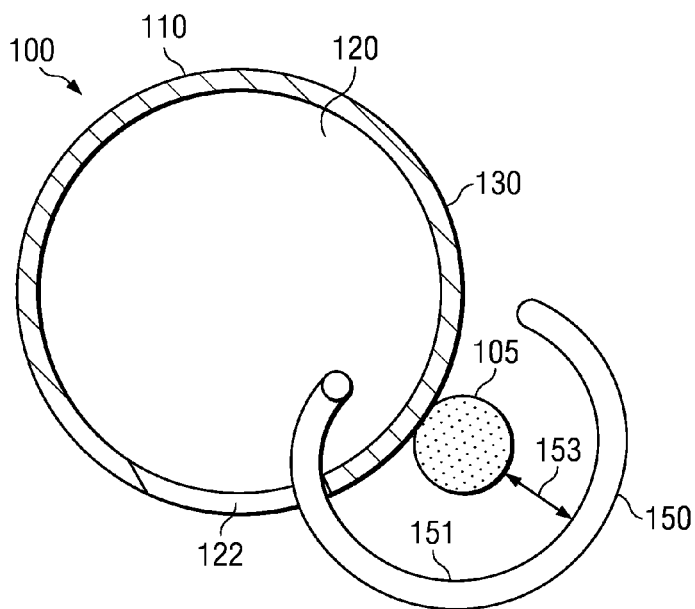
FIG. 2B shows a cross sectional view of a surgical instrument according to the teachings of the present disclosure, showing the capture wire in a deployed position.
Figure 2A:
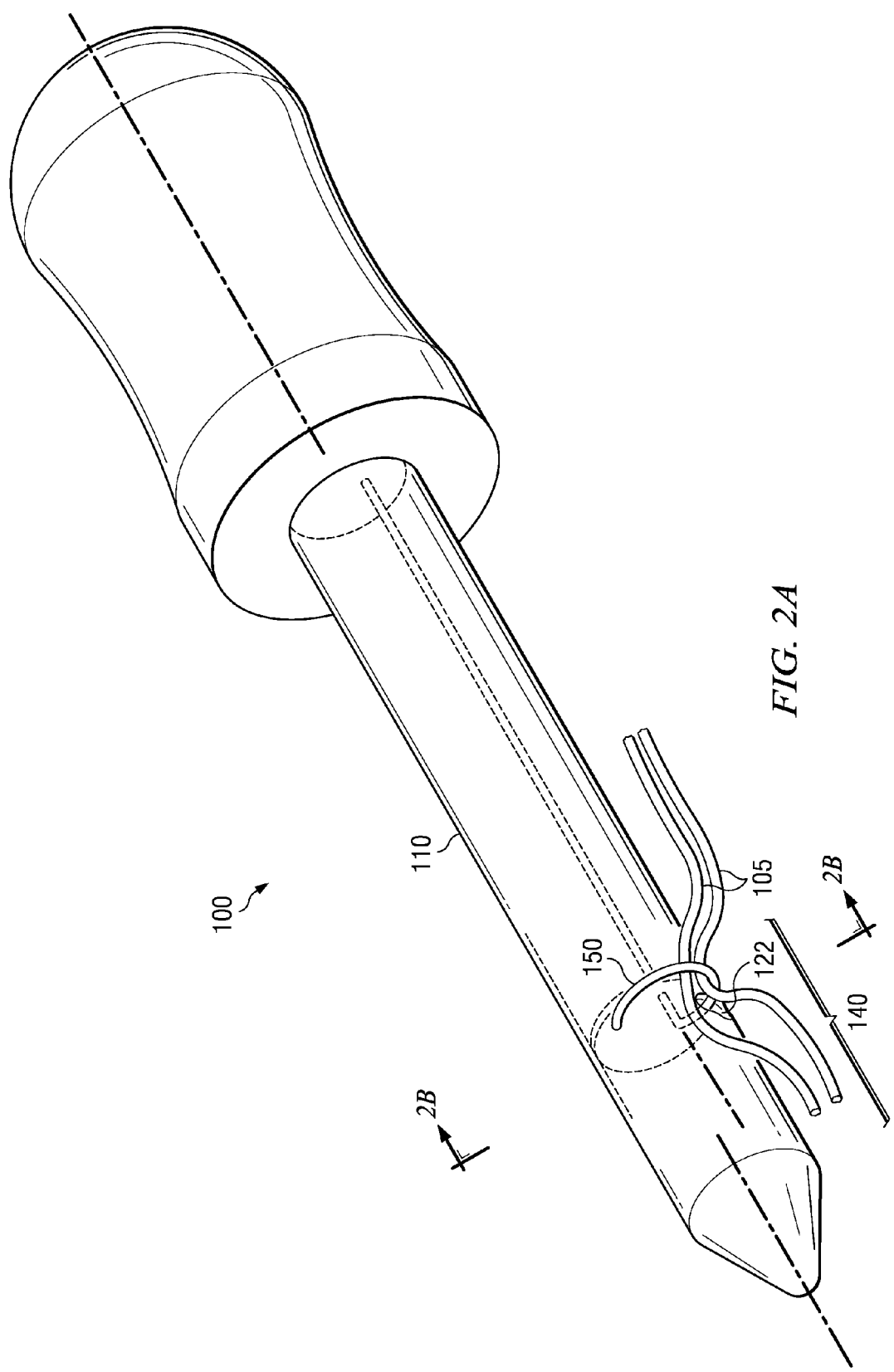
FIG. 2A shows a surgical instrument according to the teachings of the present disclosure, showing the instrument with the capture wire deployed.

FIG. 2A shows instrument 100 with wire 150 deployed and having captured suture 105. A substantial portion of wire 150 is located outside elongate body 110 and wire 150 is preformed in a curve arcuate shape so as to loop over suture 105 and hence capture suture 105. In preferable embodiments wire 150 may pinch or capture suture 105 once wire 150 is fully deployed. Instrument 100 may lock wire 150 into position once fully deployed so that wire 150 may not easily retract.

FIG. 2B shows a cross section of instrument 100, with suture 105 captured. Wire curve 151 may be preferably formed so as to easily nest within body lumen 120 and travel through aperture 122. Wire curve 151 is sized to easily loop over suture 105 without preferably interfering with or moving suture 105. Additionally curve 151 may be sized so as to create a minimal gap 153 between suture 105 and wire 150 so as to better secure capture and not allow suture 105 to easily slip. As shown, wire capture is created by trapping wire 150 between the wire 150 and outer surface 130. The concave side of wire shape may preferably face towards body outer surface 130 once wire 150 is fully deployed. It is also preferable when using instrument 100 with a cannula (not shown here) that the wire 150 size and shape when positioned outside body 110 does not prevent instrument 100 from being retracted through cannula and out of the patent cavity.

Figure 3:
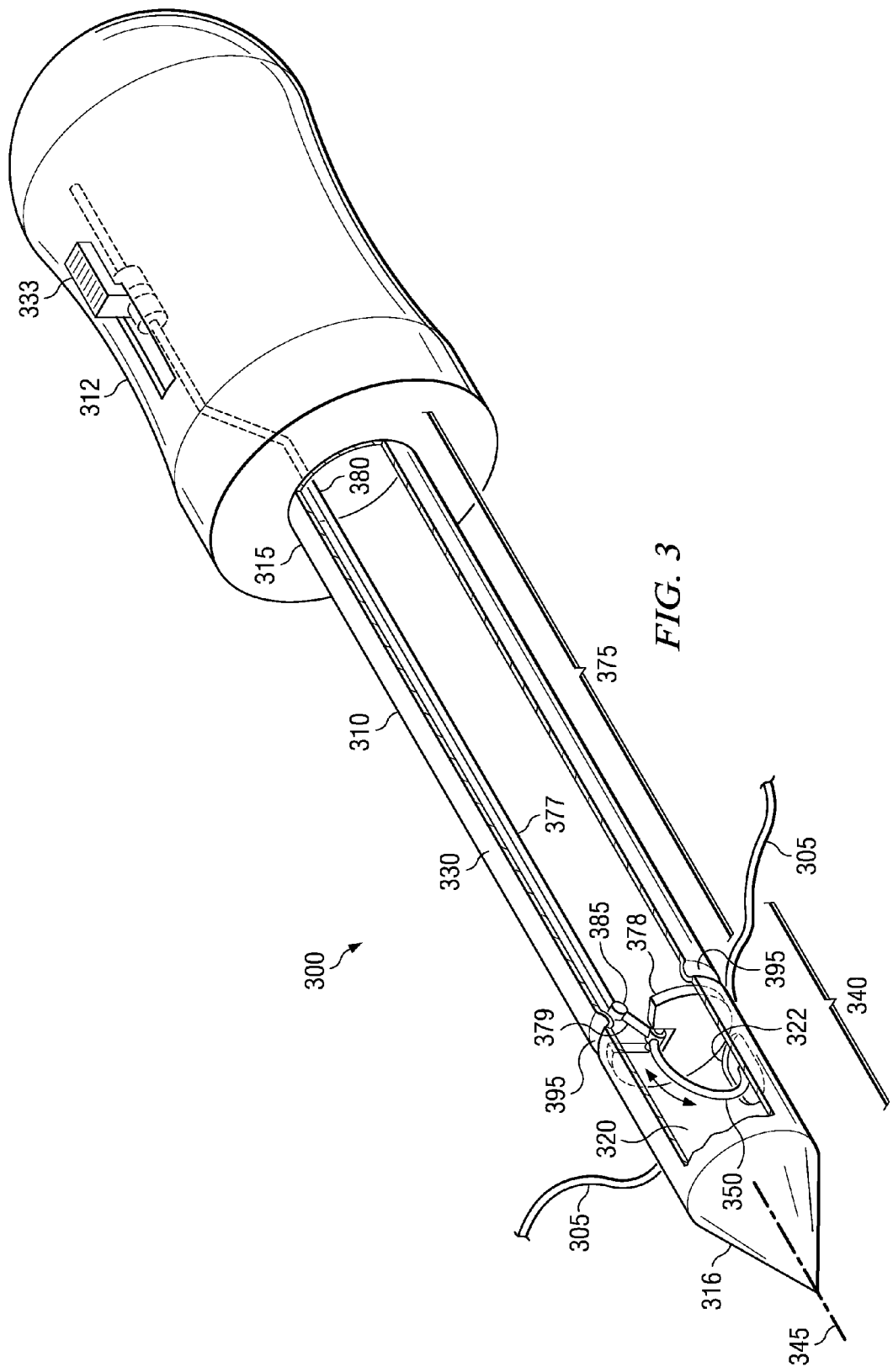
FIG. 3 shows an alternative embodiment of a surgical instrument for manipulating a surgical suture.

FIG. 3 shows an alternate embodiment of a surgical instrument 300 according to the teachings of the present disclosure. Instrument 300 includes elongate body 310 and a handle 312 located at the elongate body proximal end 315. Elongate body 310 may also include a distal portion 340, a generally smooth outer surface 330, a longitudinal axis 345 and, in certain embodiments a hollow lumen 320. Distal portion 340 may include a distal tip 316 which is generally smooth and formed to be able to puncture through the skin to access the patent cavity. Alternative embodiments may include more atraumatic distal ends 316 as previously discussed herein. Alternate embodiments may be used with an access cannula (not shown here) that provides access to the patient cavity and allowing for use of a blunter distal tip 316.

Elongate body distal portion 340 also includes at least one moveable wire 350 and at least one lateral aperture 322. Wire 350 is preferably moveable so as to be located either within elongate body lumen 320 or substantially outside elongate body distal portion 340 by traveling through aperture 322 and is moved in a way so that wire 350 eccentrically rotates. In this embodiment in FIG. 3, the motion of wire 350 is substantially coplanar with body longitudinal axis 345 and therefore may preferably capture suture 305 that is lying substantially perpendicular to longitudinal axis 345. Wire 350 is intended to move in such a way as to travel away from the outer surface 330 to loop over suture 305 and thereby capture any suture 305 that is placed close to aperture 322.

Wire 350 is moved using an actuation mechanism 375. In the present embodiment actuation mechanism 375 includes at least one pivot support 378, at least one actuation rod 377 and arm link 379. Actuation rod 377 has a proximal handle end 380 and arm link end 385. Arm link 379 connects actuation rod 377 with wire 350. Handle 312 may be connected to actuation rod handle end 380 so that actuation rod 377 may be translated back and forth along body longitudinal axis 345 to manipulate wire 350. An exemplary button 333 is shown that may be connected with handle 312 and actuation rod 377 and by sliding button 333 may translate actuation rod 377.

Translation of rod 377 may pivot arm 379 and thereby eccentrically rotate and translate wire 350 through aperture 322. In the embodiment presented here in FIG. 3 pulling actuation rod 377 towards handle 112 may move wire 350 from within elongate body 310 to outside body 310 in order to capture suture 305 between wire 350 and smooth outer surface 330 of body 310.

A trough 395 may be added to elongate body distal end 340, located around at least a portion of the circumference of elongate body 310. Trough 395 is located and shaped so as to potentially nest suture 305 in location during capture. In alternative embodiments the addition of a high friction surface to body outer surface 330 in proximity to distal portion 340 may also help to hinder the suture 305 from slipping during suture capture.

Figure 4A:
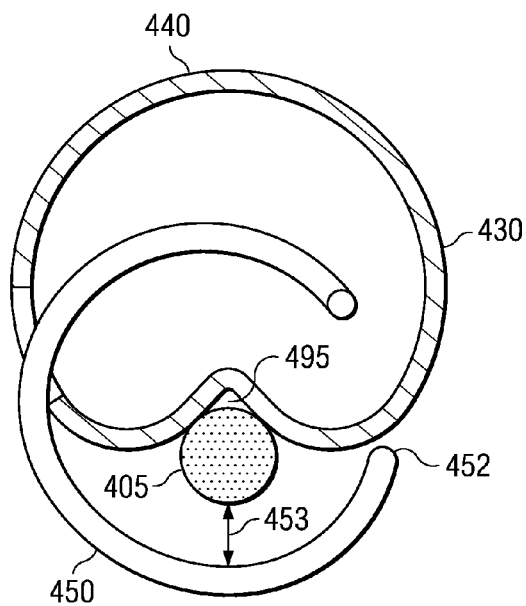
FIGS. 4A and 4B show alternative embodiments of instrument cross sectional shapes for manipulating surgical suture.
Figure 4B:
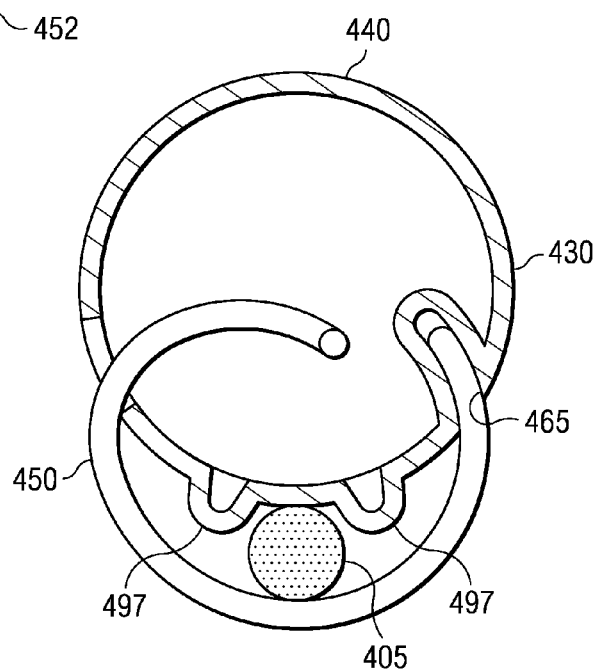

FIGS. 4A and 4B show alternate cross sectional embodiments of an elongate body 440 housing a movable wire 450 for capturing suture 405. These cross sectional embodiments are to illustrate suture movement limiters, and as shown, may be incorporated into the embodiments described above and representatively shown in FIGS. 1 and 2. FIG. 4A shows a trough 495 disposed on outer surface 430 of body 440 and is operable to receive suture 405 therein. Wire 450 may capture suture 405, aided by trough 495. Alternative embodiments may include a concave surface or concave side to elongate body 440. Wire free end 452 may also engage body outer surface 430 so that there is no gap between wire free end 452 and outer surface 430. This may improve the security of suture capture. Once wire 450 is fully deployed, gap 453 may exist, although gap 453 is preferably small so as to optimize suture 405 capture.

Additional embodiments may include at least two buttons 497 disposed on outer surface 430 of body 440 which are used to limit suture movement during suture capture as shown in FIG. 4B. Buttons 497 may be located so as to help limit suture 405 motion during capture and the location of the buttons 497 may depend on the motion of the wire 450. FIG. 4B also shows an entrance aperture or entrance funnel 465. This allows wire 450 to continue rotating and potentially better improve capture of suture 405. Entrance aperture 465 may also allow wire 450 to minimize any lateral extension of wire 450 away from body outer surface 430 which may create a lower profile and more uninterrupted outer surface 430 and allow for easier retraction through a cannula (not shown here).

Figure 5:
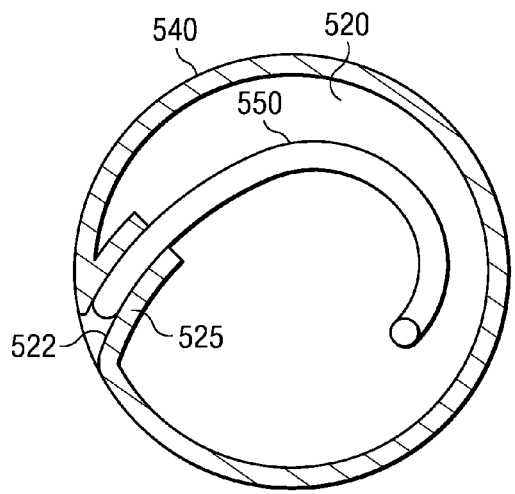
FIG. 5 shows a cross section of an instrument for manipulating surgical suture including a guiding channel.

FIG. 5 shows a cross sectional view of elongate body 540, having a guiding channel or funnel 525 at aperture 522 to aid in guiding wire 550 out of lumen 520. Guide 525 may be as long as capture wire 550 or just extend along a portion of the length of the wire 550, located closer to aperture 522.

Figure 6A:
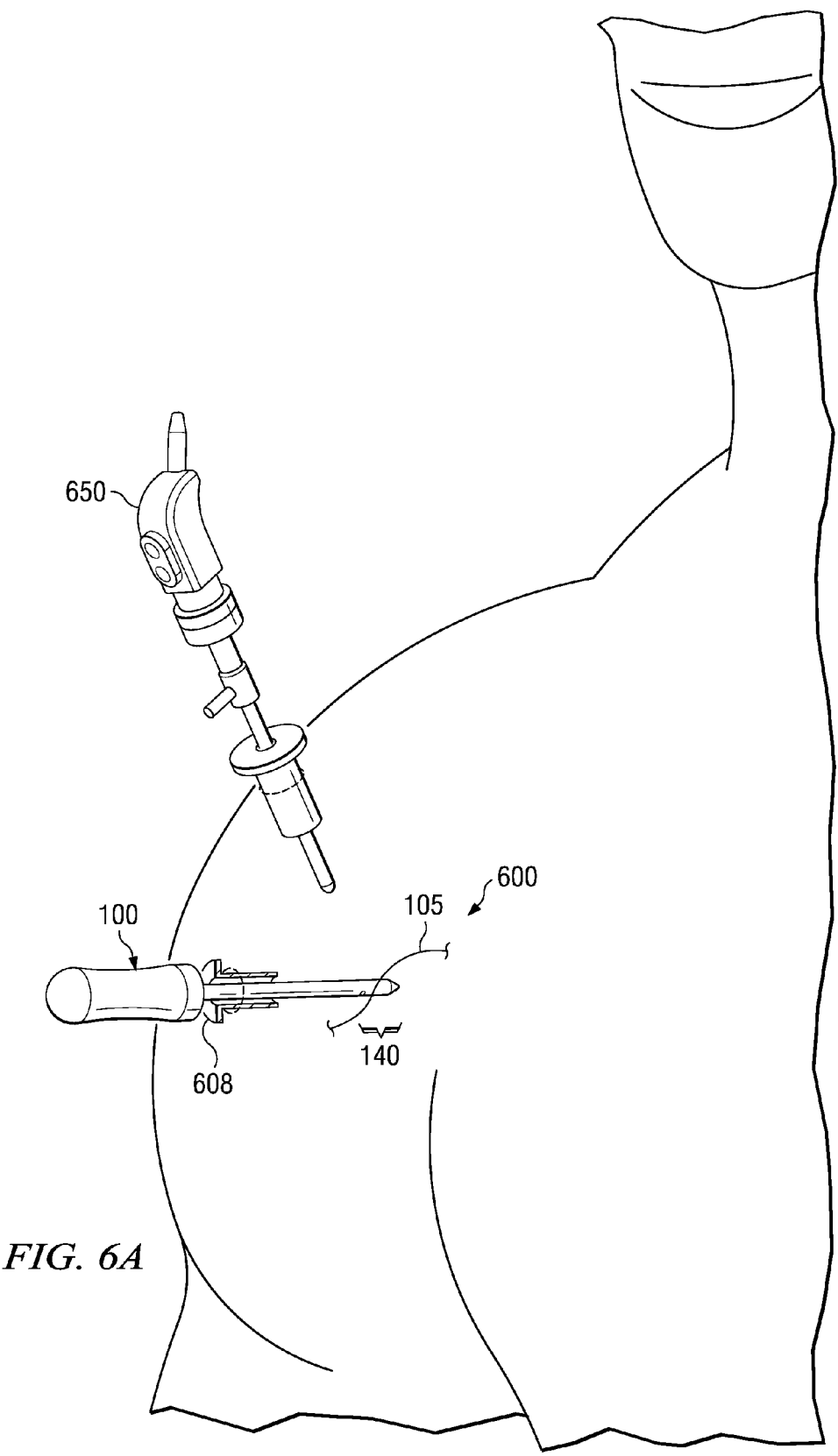
FIGS. 6A, 6B and 6C show diagrammatic representation of a method of using the surgical instrument according to the teachings of the present disclosure.
Figure 6B:
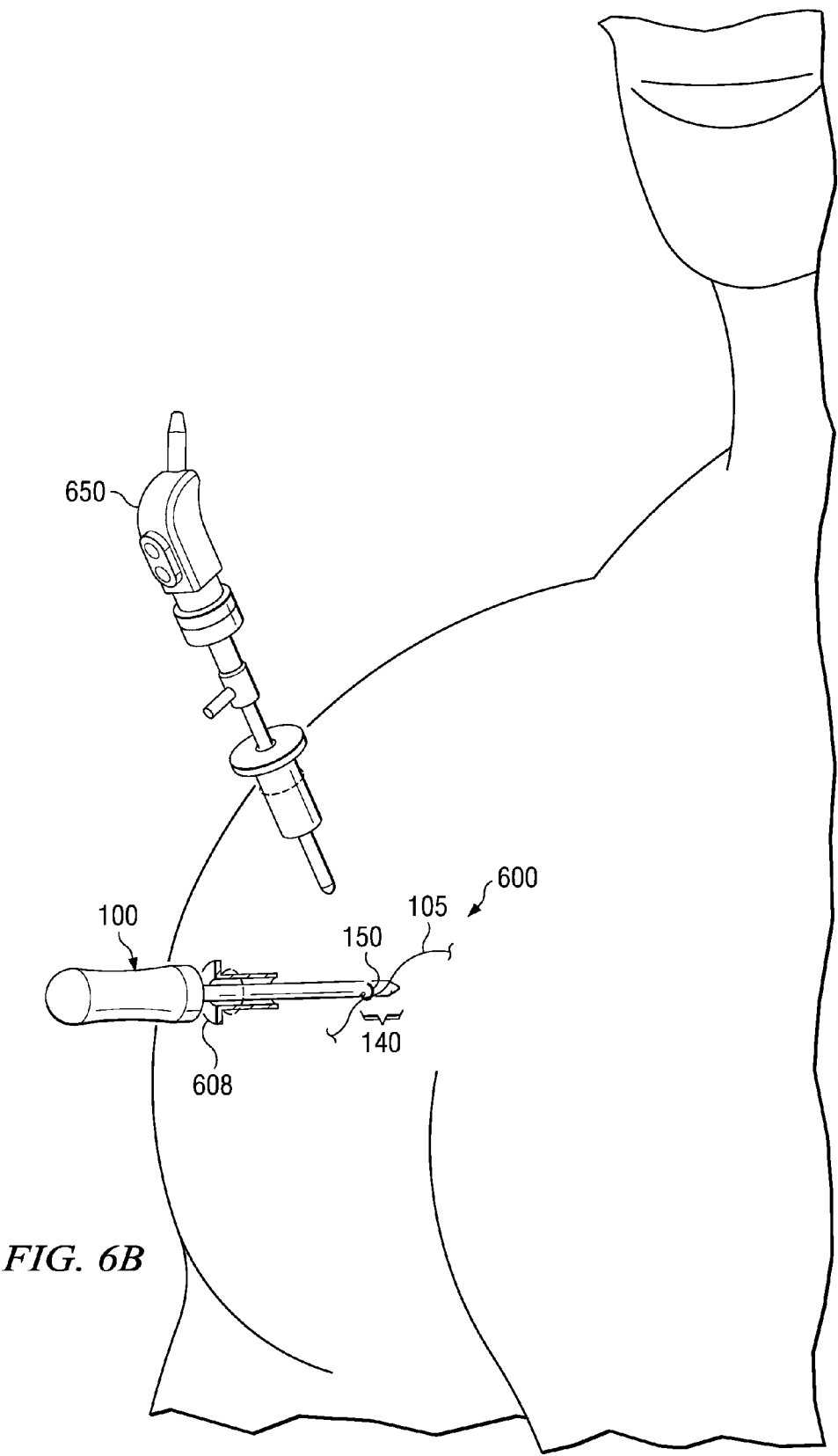
Figure 6C:
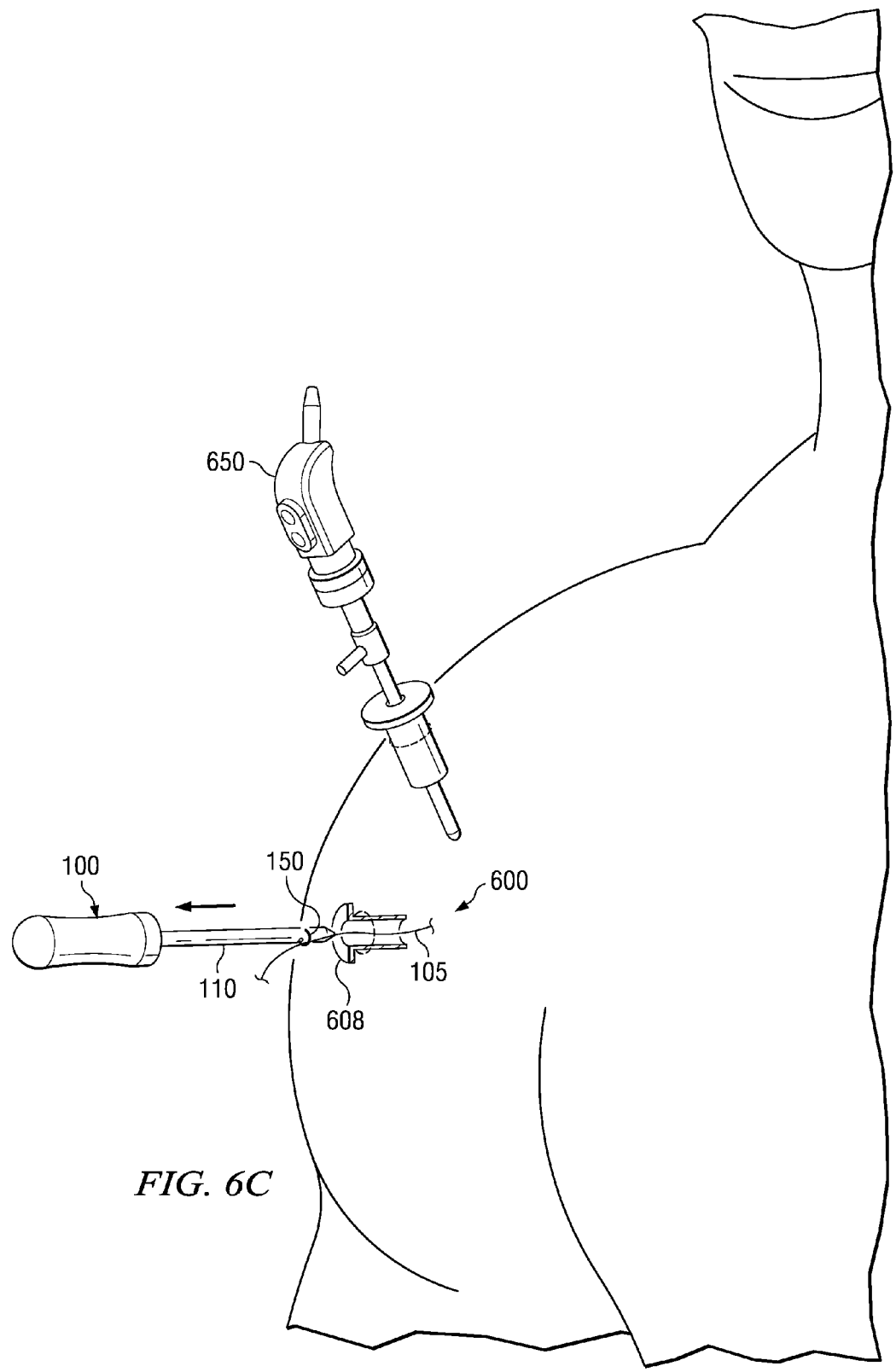

FIGS. 6A, 6B and 6C is a depiction of a method of using instrument 100 to perform a surgical procedure in accordance with teachings of the present disclosure. Instrument 100 is not illustrated to scale and is shown much larger in size than the present invention for clarity. In reality, instrument 100 may preferably be similar or smaller in diameter to imaging scope 650.

In general instrument 100 may preferably be used endoscopically and may be used in combination with a cannula 608. The present embodiment is not necessarily limited to endoscopic uses however and endoscopic surgery may also be used interchangeably with other minimally invasive procedures including but not limited to arthroscopic, percutaneous, hysteroscopic, minimally invasive or laparoscopic procedures. FIG. 6A shows instrument 100 inserted into a patient cavity 600 through cannula 608 with body distal portion 140 placed in proximity to suture 105. For exemplary purposes the present patient cavity shown is a shoulder. Visualization means such as an endoscopic camera 650 may be used to place distal tip 140 in desired location. Once distal tip 140 is in desired location and orientation with respect to suture 105, capture wire 150 may be deployed as shown in FIG. 6B, to selectively capture suture 105. Suture 105 may then be manipulated to an alternate location, inside or outside patient cavity 600 before suture 105 is released by retracting capture wire 150. FIG. 6C shows release outside patient cavity 600.

Figure 7:
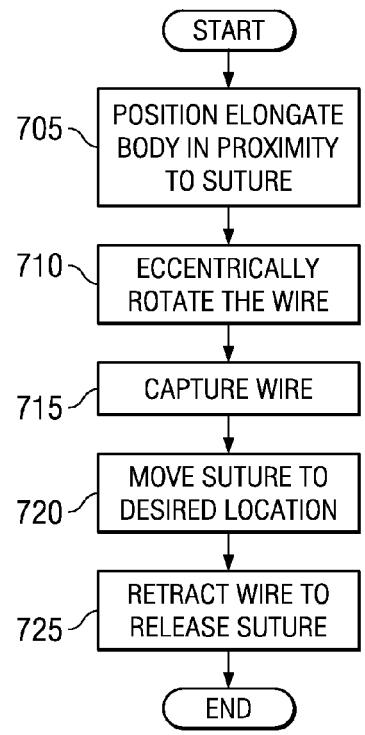
FIG. 7 shows a flow diagram of a method of performing a surgical procedure according to teachings of the present disclosure.

A method of performing a surgical procedure using surgical instrument 100 is represented schematically in FIG. 7. Instrument elongate body is first positioned in proximity to a suture (705), the elongate body having a moveable wire and an actuation mechanism disposed therein. The wire is then eccentrically rotated (710) using actuation mechanism, such that the moveable wire is deployed outside the elongate body and the suture is then captured between the moveable wire and the outer surface (715). The suture may then be moved to a desired location inside or outside patient cavity (720) and the wire may then be retracted so as to release the suture (725).

Figure 8:
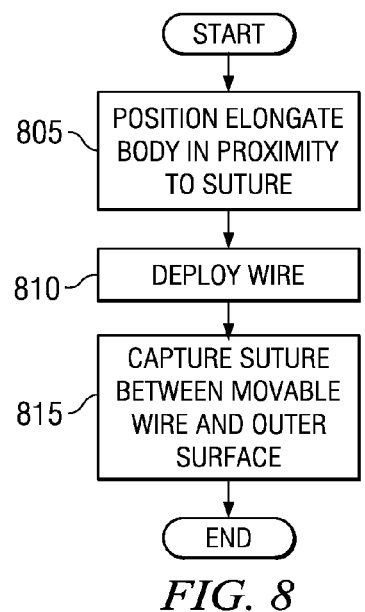
FIG. 8 shows a flow diagram of a method of performing a surgical procedure according to teachings of the present disclosure.

A method of performing a surgical procedure using surgical instrument 100 is represented schematically in FIG. 8. Instrument elongate body is first positioned in proximity to a suture (805), the elongate body having an outer surface and a moveable wire and an actuation mechanism disposed therein. The wire is then deployed (810) using actuation mechanism, such that the moveable wire is deployed outside the elongate body and the suture is then captured between the moveable wire and the outer surface (815).

Although some embodiments of the present invention have been described, it should be understood that the present invention may be embodied in many other specific forms without departing from the spirit or the scope of the present invention. Therefore, the present examples are to be considered as illustrative and not restrictive, and the invention is not to be limited to the details given herein, but may be modified within the scope of the appended claims.

What is claimed is:

1. A surgical instrument for manipulating surgical suture comprising;
   a hollow elongate body having a proximal end, a distal portion, a longitudinal axis and an outer surface;
   a handle disposed at the proximal end of the elongate body;
   at least one rigid moveable wire disposed in a first position in the distal portion of the hollow body, the wire having a free end and a connected portion, and the wire defining an arcuate portion between the free end and the connected portion; and
   an actuation mechanism coupled between the handle and the wire connected portion, the actuation mechanism eccentrically rotates the wire between the first position and a second position configure to selectively deploy and capture a suture wherein the suture is pinched between the outer surface and the wire.

2. The surgical instrument of claim 1 wherein the actuation mechanism rotates the wire about an axis that is substantially parallel to the elongate body longitudinal axis.

3. The surgical instrument of claim 1 wherein the actuation mechanism rotates the wire about an axis that is substantially perpendicular to the elongate body longitudinal axis.

4. The surgical instrument of claim 1, wherein the actuation mechanism eccentrically rotates the wire about the longitudinal axis of the elongate body.

5. The surgical instrument of claim 1, the actuation mechanism having a rotation axis, wherein the rotation axis is radially offset from the longitudinal axis of the elongate body.

6. The surgical instrument of claim 1, the actuation mechanism having a rotation axis, wherein the rotation axis nutates about an axis parallel to the longitudinal axis of the elongate body.

7. The surgical instrument of claim 1, wherein the wire is rotated and translated.

8. The surgical instrument of claim 1 wherein the actuation mechanism moves the wire so that the wire free end translates radially relative to the elongate body longitudinal axis.

9. The surgical instrument of claim 1 wherein the actuation mechanism comprises an actuation rod and said rod is rotated to move the wire.

10. The surgical instrument of claim 1 wherein the actuation mechanism comprises an actuation rod and said rod is translated to move the wire.

11. The surgical instrument of claim 1 wherein the instrument handle further comprises a knob for manipulating the actuation mechanism.

12. The surgical instrument of claim 1 wherein the elongate body outer surface further comprises at least one trough operable to limit the suture movement during suture capture.

13. The surgical instrument of claim 1 wherein the elongate body distal portion has a cross sectional shape and said cross sectional shape comprises at least one concave edge operable to limit suture movement during suture capture.

14. The surgical instrument of claim 1 wherein a portion of the elongate body outer surface has a high friction surface operable to create a frictional interface and hinder the movement of any suture during capture.

15. The surgical instrument of claim 1 wherein the elongate body distal portion comprises an aperture the aperture provides a passageway from inside the elongate body to the body outer surface for suture capture and release.

16. The surgical instrument of claim 15 wherein the aperture further comprises a guiding channel operable to guide the wire free end through the aperture.

17. The surgical instrument of claim 1 wherein the distal portion comprises at least two wires.

18. The surgical instrument of claim 17 wherein a first wire deploys in a first direction and a second wire deploys in a second direction and the first direction is substantially opposite the second direction.

19. The surgical instrument of claim 1 wherein the wire free end is movable from a first position within the elongate body distal portion to a second position outside the elongate body.

20. The surgical instrument of claim 1 wherein the wire has a cross sectional shape that has substantially flat portion.

21. The surgical instrument of claim 1, wherein the wire is actuated such that the free end engages the outer surface of body.

22. The surgical instrument of claim 1 wherein the elongate body distal portion further comprises an entrance aperture and the wire free end is adapted to enter said entrance aperture when substantially deployed.

23. The surgical instrument of claim 1 further comprising a cannula for creating a passageway for the instrument from outside a patient cavity into the patient cavity.

24. A surgical instrument for manipulating surgical suture comprising;
- a hollow elongate body having a proximal end, a distal portion, a longitudinal axis and an outer surface;
- a handle disposed at the proximal end of the elongate body;
- at least one rigid moveable wire in the distal portion of the elongate body, the wire having a free end and a connected portion, and the wire defining an arcuate portion between the free end and the connected portion; and
- an actuation mechanism coupled between the handle and the wire connected portion, the actuation mechanism operable to move the wire reversible between a first stowed position within the hollow body to a second position, where in the second position, the wire selectively captures a suture in a space between the wire and the elongated body surface wherein the suture is pinched between the outer surface and the wire.

* * * * *